United States Patent [19]

Braid

[11] 4,353,807

[45] Oct. 12, 1982

[54] LUBRICANTS AND FUELS CONTAINING BOROXAROPHENANTHRENE COMPOUNDS

[75] Inventor: Milton Braid, Haddonfield, N.J.

[73] Assignee: Mobil Oil Corporation, New York, N.Y.

[21] Appl. No.: 247,177

[22] Filed: Mar. 24, 1981

[51] Int. Cl.$^3$ ............................ C07F 5/04; C10M 1/10
[52] U.S. Cl. ........................ 252/49.6; 44/76; 260/462 C
[58] Field of Search ............ 260/462 C; 252/49.6; 44/76

[56] References Cited

U.S. PATENT DOCUMENTS 3,287,270 11/1966 McCabe ................ 260/462 C X
3,437,596 4/1969 McCabe ................ 260/462 C X
4,210,599 7/1980 Bridger ................ 260/462 C

*Primary Examiner*—Helen M. S. Sneed
*Attorney, Agent, or Firm*—Charles A. Huggett; Michael G. Gilman; James D. Tierney

[57] ABSTRACT

The present invention relates to 9-hydroxy-9,10-boroxarophenanthrene compositions which are particularly suitable additives to improve the stability of lubricating oils and fuel compositions. More particularly, esters of 9-hydroxy-9,10-boroxarophenanthrene which are formed from hindered phenols have been found to have improved and sustained oil solubility and comprise hydrolytically stable antioxidants which, in minor amounts, have been found to impart to oils of lubricating viscosity a high level of protection against oxidative degradation.

12 Claims, No Drawings

LUBRICANTS AND FUELS CONTAINING BOROXAROPHENANTHRENE COMPOUNDS

BACKGROUND OF THE INVENTION

1. Field of the Invention

The invention relates to hindered phenol esters of 9-hydroxy-9,10-boroxarophenanthrene as antioxidants and lubricant or liquid fuel compositions which contain such materials.

2. Description of the Prior Art

The present invention relates to the stabilization of lubricating and fuel compositions. More particularly, it relates to additives for lubricants and fuels which are particularly capable of inhibiting the oxidative deterioration of these materials.

The proper operation of engine parts and efficiency of mechanical systems is oftentimes hampered due to the detrimental effect of oxidation in changing the viscosity of the oil. Similarly, it is known that the oxidation of fuels, particularly during storage, causes gum formation and layer deposits which tend to cause operating malfunctions. Lubricating oils are subject to oxidative deterioration under conditions of use such as in modern internal combustion engines. Oxidation products are formed in the oil which are acidic in nature and can exert an erosive effect on metal parts with which the oil comes into contact. Furthermore, these oxidation products produce formations and deposits of varnish and sludge on the engine surfaces and, in various channels, galleries, ports and orifices. This tends to interfere with lubricating and may eventuate in the breakdown of the engine.

In accordance with the present invention, additives are provided for lubricant and fuel compositions which are capable of inhibiting the oxidative deterioration of such materials. Additionally, such additives in accordance with the present invention have been found to have an enhanced solubility in lubricating oils. Of particular significance, in accordance with the present invention, is the ability to improve the friction and oxidation properties of oleaginous materials such as lubricating media which may comprise either a mineral oil or a synthetic oil, or a grease therefrom. In general, mineral oils, both paraffinic, naphthenic and mixtures thereof, employed as the lubricant or grease vehicle, may be of any suitable lubricating viscosity range, as for example, from about 45 SSU at 100° F. to about 600 SSU at 100° F., and preferably, from about 50 to about 250 SSU at 100° F. These oils may have viscosity indexes ranging to about 100 or higher. Viscosity indexes from about 70 to about 95 are preferred. The average molecular weights of these oils may range from about 250 to about 800.

In instances where synthetic oils are desired in preference to mineral oils, or in combination therewith, various compounds of this type may be successfully utilized. Typical synthetic vehicles include polyisobutylene, polybutenes, hydrogenated polyolefins, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenol) ether, phenoxy phenylethers. It is to be understood, however, that the compositions contemplated herein can also contain other materials. For example, corrosion inhibitors, extreme pressure agents, viscosity index improvers, co-antioxidants, anti-wear agents and the like can be used. These materials do not detract from the value of the compositions of this invention, but rather they serve to impart their customary properties to the particular compositions in which they are incorporated.

It has been found that the additives of the present invention are highly effective antioxidants which remain effective and soluble in the oil fraction even in the presence of water, e.g. in oil-water emulsion formulations. The prior art teaches the employment of compositions such as 9-hydroxy-9,10-boroxarophenanthrene as additives to impart antioxidation characteristics to lubricants and fuels. For example, in accordance with the teachings contained in U.S. Pat. No. 3,287,270, the disclosure of which is incorporated herein by reference, 9-hydroxy-9,10-boroxarophenanthrenes are disclosed as being capable of improving the oxidative resistance of lubricant and fuel compositions.

These 9-hydroxy-9,10-boroxarophenanthrene compounds and certain derivatives thereof may be represented by the general formula

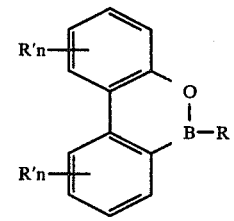

where R represents hydroxy, hydrocarbyl, hydrocarbyloxy, halogen, halogenated hydrocarbyl, halogenated hydrocarbyloxy groups or, in the case of the anhydride, a 9,10-boroxarophenanthryloxy group; R' represents the same or different hydrocarbyl, halogen or halogenated hydrocarbyl groups; wherein such groups contain from 1 to 30 and preferably from 1 to 18 carbon atoms; and n may be 0 or an integer from 1 to 4, preferably 1 or 2.

Although the foreging compounds, derivatives of 9-hydroxy-9,10-boroxarophenanthrene, are effective antioxidants in oils of lubricating viscosity and greases, it has been found that the utility of such compounds is circumscribed in many applications because of their low oil solubility. 9-Hydroxy-9,10-boroxarophenanthrene readily dehydrates to form an anhydride which has slightly better oil solubility and other borate esters may also be made as hereinbefore disclosed in order to improve oil solubility. However, the anhydride and such esters are all extremely prone to hydrolysis thus liberating the poorly soluble 9-hydroxy-9,10-boroxarophenanthrene which is precipitated from the oil depriving it of oxidation protection. Thus, they have a tendency to lose most of their stabilizer effectiveness.

SUMMARY OF THE INVENTION

It has now been found that when an ester of 9-hydroxy-9,10-boroxarophenanthrene is made with a hindered phenol, that is a phenol in which both ring positions adjacent to the hydroxyl group are substituted by bulky hydrocarbyl groups, such as 2,6-di-tertiarybutyl-4-methylphenol, 2,4,6-tri-tertiary-butylphenol and the like, that the solubility of the resulting compounds is vastly improved. Moreover, the resulting additive is a surprisingly effective antioxidant which remains effective and oil-soluble even in the presence of water, e.g. in oil-water emulsion formulations or water available from co-additives, or generated during oxidation, or water available from exposure to atmospheric moisture.

Although esters of 9-hydroxy-9,10-boroxarophenanthrenes have been disclosed in the prior art, hindered phenol esters of such compounds and lubricant compositions containing them are unique. The prior art disclosures clearly define the limitation of one hindered phenol ester group regardless of large stoichiometric excesses of hindered phenol reactants, in the preparation of borate esters regardless of whether such esters are made by the replacement of relatively small alkyl groups from trialkyl borates such as trimethyl borate or by direct esterification of boric acid. The presence of a single hindered phenyl group in a borate ester is sufficient to preclude any further esterification or transesterification by a second physically large reactant. In view of the steric resistance to further esterification provided by a hindered phenyl group, it would not be obvious that the large polynuclear heterocyclic 9-hydroxy-9,10-boroxarophenanthrene system could sterically accommodate or permit esterification by a hindered phenol. Thus, compounds in accordance with the present invention comprise hindered phenol esters formed by the reaction of, for example, 9-hydroxy-9,10-boroxarophenanthrene with a hindered phenol, such as 2,6-di-tertiary-butyl-4-methylphenol or 2,4,6-tri-tertiary-butylphenol. The following structural formula is representative of these compounds:

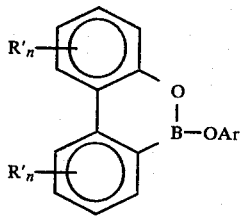

wherein Ar is an aromatic moiety derived from a hindered phenol. More specifically, Ar is derived from a hindered phenol in which the two positions ortho or adjacent to the carbon bonded to the oxygen atom are substituted by bulky alkyl or aralkyl groups which sterically interfere with access to the oxygen atom and its bonded hydrogen atom so as to prevent normal participation of the phenolic hydroxyl group in reactions, such as with sodium hydroxide to form the sodium phenoxide salt in an acid-base reaction or in physical associations, e.g. hydrogen bonding. $R'_n$ has been defined hereinbefore.

Examples of hindered phenols which may be employed to obtain compositions of the structure as hereinabove represented may be illustrated by the following structural formula

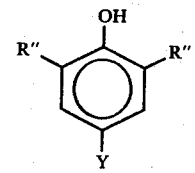

in which R" may be an alkyl or aralkyl group in which the carbon bonded to the ring carbon is itself bonded to at least two other carbon atoms and which contains from about $C_3$ up to about $C_{20}$ carbon atoms in any isomeric arrangement consistent with the limitations hereinabove discussed. Y in the above structural formula may be hydrogen, an alkyl group of from 1 up to 20 carbon atoms in any isomeric arrangement, an alkoxy or carbalkoxy group and the like, containing in the alkoxy portion of the structure from 1 to 20 carbon atoms.

From the foregoing, it will be seen that the compositions of the present invention may be readily tailored to improve their solubility as well as their compatibility with particular base stocks.

DESCRIPTION OF THE SPECIFIC EMBODIMENTS

The preparation of the 9,10-boroxarophenanthrene reactants employed in the present invention is, in general, known to the art. For example, the methods described by Dewar and Dietz, Journal Chemistry Society (London), 1344 (1960), which reference is incorporated herein by reference, may be employed.

The preparation of 9-hydroxy-9,10-boroxarophenanthrene is exemplary of these procedures. Briefly, ortho-phenylphenol (1) is reacted with excess boron trichloride. The intermediate product (2) from the reaction is then heated in the presence of aluminum chloride to give 9-chloro-9,10-boroxarophenanthrene (3). This chloro compound is then treated with water to give the desired 9-hydroxy-9,10-boroxarophenanthrene (4). Although the present invention is not limited to any particular theory, it is believed that the above reactions may be represented as follows:

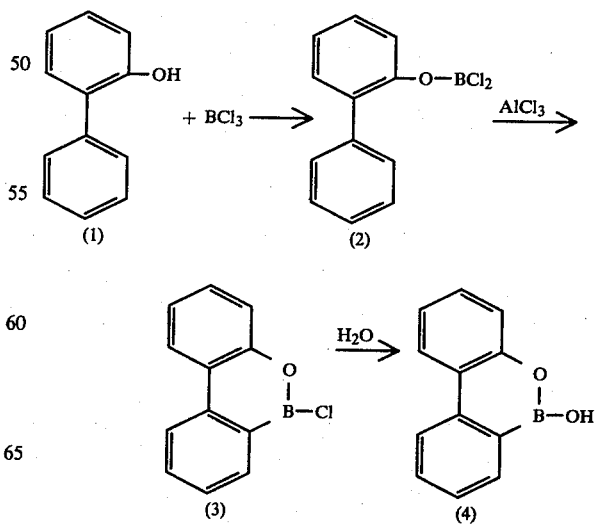

The hindered phenol borate esters of the present invention may then be represented by the following structural formula

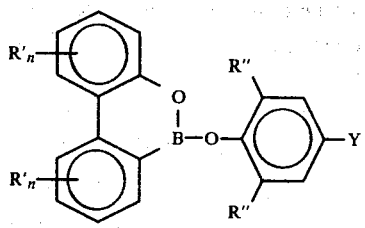

The hindered phenol ester of the aforedescribed 9-hydroxy-9,10-boroxarophenanthrene compounds may be prepared in accordance with the reaction conditions as outlined in the following Example wherein 9-hydroxy-9,10-boroxarophenanthrene is reacted with a large excess of a 2,6-di-tertiary-butylphenol to form an example of a hindered phenol borate ester of the present invention.

EXAMPLE 1

A benzene solution of 9-hydroxy-9,10-boroxarophenanthrene was added slowly to an excess of 2,6-di-tertiary-butyl-4-methylphenol heated at 225°–230° C. Only a minor amount of the anhydride of 9-hydroxy-9,10-boroxarophenanthrene (pentane insoluble) was formed. The major product was the hindered phenol borate ester, 2,6-di-tertiary-butyl-4-methylphenoxy-9,10-boroxarophenanthrene. The product was soluble in oil, up to 2% and is a very effective antioxidant in the catalytic oxidation test as shown in the following Table 1.

In order to evaluate the antioxidant properties of the hindered phenol borate esters prepared in accordance with the preceding example, oil compositions containing these compounds are prepared and subjected to a catalytic oxidation test. The test procedure is as follows:

EVALUATION OF PRODUCTS

The hindered phenol borates of this invention were tested in a Catalytic Oxidation Test for lubricants, using as the base medium a lubricant. The test lubricant composition is subjected to a stream of air which is bubbled through the composition at a rate of 5 liters per hour at 325° F. for 40 hours. Present in the composition are metals commonly used as materials of engine construction, namely:

(a) 15.6 sq. in. of sand-blasted iron wire,
(b) 0.78 sq. in. of polished copper wire,
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number (ΔNN) and kinematic viscosity (ΔKV) occasioned by the oxidation. Compounds in accordance with this invention tested for their oxidative stabilizing properties in accordance with the above Catalytic Oxidative Test proved highly effective oxidation stabilizers and/or inhibitors.

In assessing the results of this test, it will be understood that the more important consideration is the control of viscosity increase.

TABLE 1

| Additive | Additive Concentration (Wt. %) | NN | % KV Increase |
|---|---|---|---|
| Example 1 | 2.0 | 0.5 | 1.50 |
|  | 1.0 | 0.7 | 20 |
|  | 0.5 | 6.9 | 78 |
| Example 2 | (Base Oil)* | 17 | 334 |

*The base oil employed in the preceding examples was a neutral, solvent refined, mineral base oil having a viscosity at 100° F. of 130 SUS.

Particularly preferred hindered phenyl esters of 9-hydroxy-9,10-boroxarophenanthrene which may be employed in the present invention include esters of 2,4,6-tri-tertiary-butylphenol and 2,6-di-tertiary-butyl-4-methylphenol. Other hindered phenols may be employed as hereinbefore described and as will be apparent to those skilled in the art.

Certain modifications of the invention will become apparent to those skilled in the art and the illustrated details disclosed are not to be construed as imposing unnecessary limitations on the invention.

What is claimed is:
1. A compound of the formula

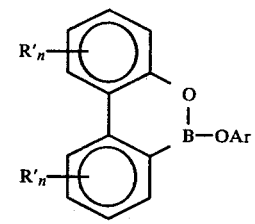

wherein R' is a hydrocarbyl group containing 1 to 30 carbon atoms, n may be 0 or an integer of 1 to 4, and Ar is an aromatic moiety derived from a hindered phenol.

2. The compound of claim 1 wherein Ar is

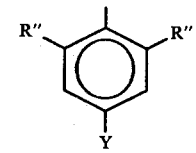

and where R" is an alkyl or aralkyl group, in which the carbon bonded to the ring carbon is itself bonded to at least two other carbon atoms, and which contains 3 to 20 carbon atoms and Y is hydrogen, an alkyl group of from 1 to 20 carbon atoms, an alkoxy group, a carbalkoxy group, the alkoxy and carbalkoxy groups containing 1 to 20 carbon atoms.

3. The compound of claim 2 wherein R" is an alkyl group.

4. The compound of claim 3 wherein R" is the tertiarybutyl group.

5. A lubricant or liquid hydrocarbon fuel composition comprising a major proportion of a lubricant or liquid hydrocarbon fuel and an antioxidant amount of the compound of claim 1.

6. A lubricant or liquid hydrocarbon fuel composition comprising a major proportion of a lubricant or fuel and an antioxidant amount of the compound of claim 2.

7. A lubricant or liquid hydrocarbon fuel composition comprising a major proportion of a lubricant or fuel and an antioxidant amount of the compound of claim 3.

8. A lubricant or liquid hydrocarbon fuel composition comprising a major proportion of a lubricant or fuel and an antioxidant amount of the compound of claim 4.

9. The composition of claims 5, 6, 7 or 8 wherein said lubricant is a mineral oil.

10. The composition of claims 5, 6, 7 or 8 wherein said lubricant is a synthetic oil.

11. The composition of claims 5, 6, 7 or 8 wherein said lubricant is a mixture of mineral and synthetic oils in the combination mineral-mineral, synthetic-synthetic or mineral-synthetic.

12. The composition of claims 5, 6, 7 or 8 wherein said lubricant is a grease.

* * * * *